(12) United States Patent
Handa et al.

(10) Patent No.: US 7,041,826 B2
(45) Date of Patent: May 9, 2006

(54) PROCESS FOR PREPARING 1-METHYL-3-PHENYLPIPERAZINE USING A NOVEL INTERMEDIATE

(75) Inventors: Vijay Kumar Handa, Hyderabad (IN); Divvela Venkata Naga Srinivasa Rao, Hyderabad (IN); Meenakshisunderam Sivakumaran, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 307 days.

(21) Appl. No.: 10/648,636

(22) Filed: Aug. 26, 2003

(65) Prior Publication Data

US 2004/0242879 A1    Dec. 2, 2004

(30) Foreign Application Priority Data

Jun. 2, 2003    (IN)    ............... 442/MAS/2003

(51) Int. Cl.
C07D 241/04    (2006.01)
C07D 295/00    (2006.01)

(52) U.S. Cl. ...................... 544/384; 544/403
(58) Field of Classification Search ........ 544/384, 544/403
See application file for complete search history.

(56) References Cited

U.S. PATENT DOCUMENTS 4,772,705 A * 9/1988 Schmiesing ................ 544/344

FOREIGN PATENT DOCUMENTS

| CA | 2 370 389 | * 10/2000 |
| CA | 2 4690 571 | * 3/2003 |
| CH | 520 693 | * 3/1972 |
| WO | WO 02/090339 | * 11/2002 |

OTHER PUBLICATIONS

Guo et al, "An Efficient Process for Preparing 4-Methyl-2-phenyl Piperazine Hydrochloride and its Derivatives" Chinese Chemical Letters, vol. 14(4), pp. 365-367 (2003).*

Ikeda et al, "Piperazine Compounds. VI. Antihistaminic and Anticholinergic Effects of 2-Phenylpiperazine Derivatives" Yakugaku Zasshi, vol. 90(11), pp. 1452-1456 (1970).*

Roderick et al, "Derivatives of Piperazine. XXXV. Synthesis of 2-Phenylpiperazine and Some Derivatives" Journal of Medicinal Chemistry, vol. 9(2), pp. 181-185 (1965).*

Haberl, R. "Über die Herstellung C-methyl-phenyl-substituierter Piperazine" Monatshefte für Chemie, vol. 89 (6), pp. 798-805 (1958).*

* cited by examiner

Primary Examiner—James O. Wilson
Assistant Examiner—Zachary C. Tucker
(74) Attorney, Agent, or Firm—Jay R. Akhave

(57) ABSTRACT

The present invention describes an industrially advantageous process to prepare highly pure 1-Methyl-3-phenylpiperazine of Formula I

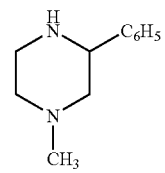

Formula I that makes use of a novel piperazine derivative, 4-Benzyl-1-methyl-2-oxo-3-phenylpiperazine, represented by Formula II

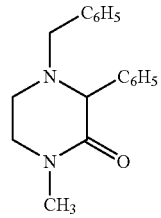

Formula II 1-Methyl-3-phenylpiperazine is a useful intermediate in the preparation of antidepressant Mirtazapine.

13 Claims, No Drawings

PROCESS FOR PREPARING 1-METHYL-3-PHENYLPIPERAZINE USING A NOVEL INTERMEDIATE

BACKGROUND OF THE INVENTION

Mirtazapine, also known as 2-methyl-1,2,3,4,10,14b-hexahydrobenzo[c]pyrazino-(1,2-a) pyrido[3,2-f]azepine, is an antidepressant drug suitable for oral administration. Mirtazapine belongs to piperazinoazepine group of compounds and has the following chemical structure.

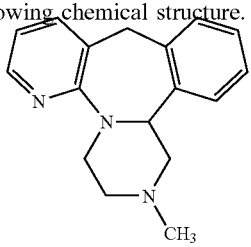

1-Methyl-3-phenylpiperazine is the key intermediate in the preparation of Mirtazapine. U.S. Pat. No. 4,062,848 has described the synthesis of Mirtazapine using 1-Methyl-3-phenylpiperazine as starting material. It is believed that the earliest synthesis of this key intermediate is that of Roderick et. al., J. Med. Chem. 1966, 181–185. This publication has reported the preparation of 1-Methyl-3-phenylpiperazine starting from α-bromophenylacetic acid ester and ethylenediamine resulting in the formation of 2-oxo-3-phenylpiperazine which is then subjected to lithium aluminium hydride reduction and subsequently methylated with methyl iodide and triethylamine in acetone.

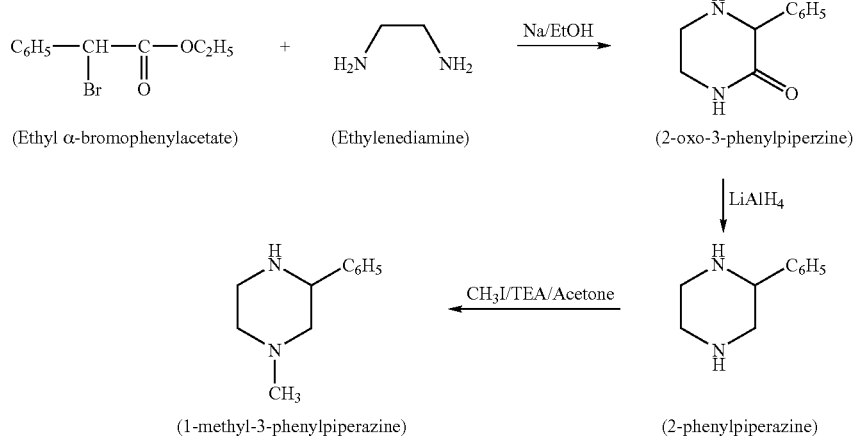

The drawback of this method is the non-selective methylation at 1-position. A mixture of products like unreacted 2-phenylpiperazine, 1-methyl-2-phenylpiperazine and 1,4dimethyl-2-phenylpiperazine alongwith the desired 1-Methyl-3-phenylpiperazine is obtained. Therefore, extensive purification is required to obtain pure 1-Methyl-3-phenylpiperazine.

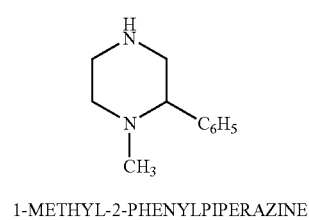

1-METHYL-2-PHENYLPIPERAZINE

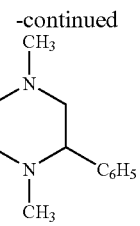

1,4-DIMETHYL-2-PHENYLPIPERAZINE

U.S. Pat. No. 6,495,685 has described the preparation of 1-Methyl-3-phenylpiperazine by reacting N-(2-chloroethyl)-N-methyl-β-chloro-β-phenylethylamine (the dichloride) of Formula III with ammonia.

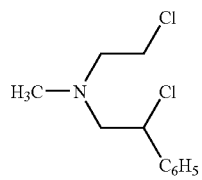

Formula III

This dichloride of Formula III has been prepared by chlorination of the corresponding diol, N-(2-hydroxyethyl)-N-methyl-β-hydroxy-β-phenylethylamine of Formula IV.

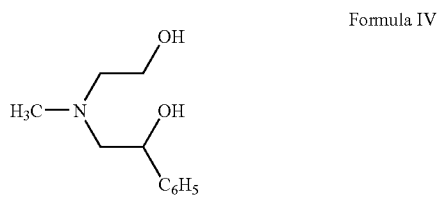

Formula IV

In U.S. Pat. No. 6,495,685, this diol has been obtained by reacting styrene oxide with N-methylethanolamine. However, the described preparation of diol results in the formation of substantial amount of isomeric compound of Formula V due to non-selectivity in this reaction.

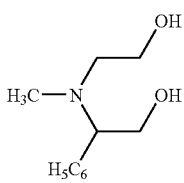

Formula V

The presence of isomeric diol of Formula V results in the formation of corresponding 1-methyl-2-phenylpiperazine isomer which contaminates the product and results in lower productivity.

Next, the same dichloride of Formula III has been treated with p-toluenesulfonamide in the U.S. Pat. No. 6,339,156 to obtain tosyl piperazine which is hydrolyzed to produce 1-Methyl-3-phenylpiperazine. However, preparation of dichloride and its isomeric purity has not been discussed in this US patent.

In view of the prior art described above, the present invention provides a new process for preparing highly pure 1-Methyl-3-phenylpiperazine where the formation of 2-phenylpiperazine, 1-methyl-2-phenylpiperazine isomer and 1,4-dimethyl-2-phenylpiperazine has been avoided.

DETAILED DESCRIPTION OF THE INVENTION

The present invention relates to a new process for preparing highly pure 1-Methyl-3-phenylpiperazine suitable for use in the synthesis of Mirtazapine and other tetracyclic compounds. The present invention also relates to a novel intermediate used to carryout this process.

According to the present invention, there is provided a process for preparing a novel compound, 4-Benzyl-1-methyl-2-oxo-3-phenylpiperazine, of Formula II

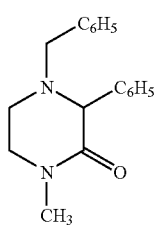

Formula II by methylation of 4-benzyl-2-oxo-3-phenylpiperazine of Formula VI

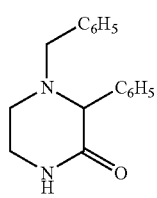

Formula VI with methyl iodide in N,N-dimethylformamide in presence of sodium hydride. Typically, the methylation is carried out with 1.1 to 1.2 moles of methyl iodide and sodium hydride each per one mole of compound of Formula VI. It is preferred to carryout the methylation by adding compound of Formula VI to the sodium hydride slurry in N,N-dimethylformamide followed by methyl iodide addition. The temperature during methylation is maintained at 10° C. to 25° C. and usually it takes 1 hour to complete the reaction.

Reduction of the above mentioned novel piperazine compound is carried out with lithium aluminium hydride in tetrahydrofuran to obtain protected piperazine of Formula VII.

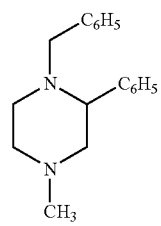

Formula VII

This reduction is accomplished with 1.0–1.2 mole of lithium aluminium hydride per mole of the compound of Formula VI at a temperature 40° C. to 70° C. and preferably at the reflux temperature.

Finally, 1-Methyl-3-phenylpiperazine of Formula I is obtained by removing benzyl protecting group through catalytic hydrogenation. The deprotection is performed by dissolving the compound of Formula VII in acetic acid and subjecting it to hydrogenation at 20° C. to 30° C. in the presence of 5% palladium-carbon catalyst. The hydrogen pressure is maintained at 80 psi to 100 psi. End point of the reaction is readily confirmed by high performance liquid chromatography and thereafter acetic acid is removed by distillation. An aqueous alkali such as sodium hydroxide is added to the reaction mass containing 1-Methyl-3-phenylpiperazine of Formula I thus obtained to make the solution alkaline, for instance, to pH 11.0 to 12.0. 1-Methyl-3-phenylpiperazine can be isolated by extracting with toluene, methylene chloride, ethyl acetate, cyclohexane or the like, preferably with toluene and thereafter distilling the extract.

Alternatively, compound of Formula II can be deprotected to produce compound of Formula VIII

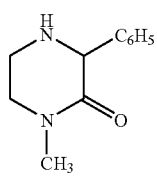

Formula VIII which subsequently subjected to lithium aluminium hydride reduction to obtain 1-Methyl-3-phenylpiperazine.

The major advantage of the present invention is that 1-Methyl-3-phenylpiperazine thus obtained contains none of the impurities like 2-phenylpiperazine, 1-methyl-2-phenylpiperazine isomer and 1,4-dimethyl-2-phenylpiperazine.

1-Methyl-3-phenylpiperazine as obtained by the method described in this invention can be used in the preparation of Mirtazapine.

The invention is further illustrated by the following examples.

EXAMPLE 1

PREPARATION OF 4-BENZYL-1-METHYL-2-OXO-3-PHENYLPIPERAZINE 15.3 g of sodium hydride (65% dispersion in mineral oil, 0.414 moles) was suspended in 250 ml of N,N-dimethylformamide at 10° C. To this suspension, 100 g of 4-benzyl-2-oxo-3-phenylpiperazine (0.376 moles) was added portionwise over a period of 30 min and stirred for 15 min. A solution of 64 g of methyl iodide (0.45 moles) in 50 ml of N,N-dimethylformamide was added slowly in 45 min maintaining the temperature below 25° C. and maintained for 1 hour. After completion of the reaction, mass was poured slowly in 1000 ml of cold water (15° C.). The product was extracted with toluene (1×500 ml, 1×300 ml) from aqueous phase. Toluene layer was washed with water (2×200 ml) and concentrated. To the residue, 250 ml of cyclohexane was added and cooled to 10° C. with stirring. Filtered the product and washed with precooled cyclohexane to obtain 98.5 g of 4-benzyl-1-methyl-2-oxo-3-phenylpiperazine product (yield: 93.8%, purity: 99.15 by HPLC)

MASS: m/z; 281.0 [(MH)$^+$]$^1$H NMR (300 MHz) in CDCl$_3$: δ(ppm); 2.49–2.57 (m, 1H), 2.97 (s, 3H), 2.99–3.03 (m, 1H), 3.14–3.18 (m, 2H), 3.54–3.77 (m, 2H), 4.06 (s, 1H), 7.21–7.53 (m, 10H).

EXAMPLE 2

PREPARATION OF 4-BENZYL-1-METHYL-3-PHENYLPIPERAZINE 14.62 g of lithium aluminium hydride (0.385 moles) was suspended in 450 ml of tetrahydrofuran at 15° C. under nitrogen atmosphere. 90 g of 4-benzyl-1-methyl-2-oxy-3-phenylpiperazine (0.321 moles) was added slowly in 1 hour at 10–15° C. The reaction mass was refluxed for 6 hours. Thereafter, the reaction mass was cooled to 5° C. and quenched successively with 15 ml of water, 15 ml of 15% aqueous sodium hydroxide solution, 45 ml of water. The reaction mass was stirred for 1 hour at 20–25° C., filtered and residue was washed with tetrahydrofuran (2×90 ml). The filtrate was concentrated and 300 ml of water was added. Filtered the product, washed with water and dried under reduced pressure to obtain 80 g of the title compound (yield: 93.6%).

$^1$H NMR (300 MHz) in CDCl$_3$: δ(ppm); 2.08–2.24 (m, 3H), 2.27 (s, 3H), 2.73–2.88 (m, 4H), 3.39–3.44 (m, 1H), 3.79–3.83 (m, 1H), 7.17–7.50 (m, 10H).

PREPARATION OF 1-METHYL-3-PHENYLPIPERAZINE 60 g of 4-benzyl-1-methyl-3-phenylpiperazine (0.226 moles) obtained above was dissolved in acetic acid (300 ml) and 3 g of 5% palladium on charcoal (50% wet) was added and the reaction mass was subjected to hydrogenation at 80–100 psi for 4 hours at 25–30° C. After completion of the reaction by HPLC, the reaction mixture was filtered and acetic acid was concentrated under reduced pressure. 150 ml of water was added to dissolve the residue and washed with 60 ml of toluene. pH was adjusted to 11.0–12.0 with 50% sodium hydroxide solution and the product was extracted with toluene (1×300 ml, 1×180 ml). Toluene was concentrated under reduced pressure and highly pure title compound was isolated in cyclohexane (80 ml, 10° C.) having HPLC purity 100%.

m.p.: 58–60° C.

MASS: m/z; 177.0 [(MH)$^+$]$^1$H NMR (300 MHz) in CDCl$_3$: δ(ppm); 1.76 (bs, 1H), 1.93–2.16 (m, 2H), 2.29 (s, 3H), 2.76–3.07 (m, 4H), 3.85–3.86 (m, 1H), 7.21–7.39 (m, 5H).

EXAMPLE 3

PREPARATION OF 1-METHYL-2-OXO-3-PHENYLPIPERAZINE

4-Benzyl-1-methyl-2-oxo-3-phenylpiperazine (15 g, 0.535 moles) was dissolved in acetic acid (120 ml) and added 5% palladium-carbon (50% wet, 1.5 g). Reaction mass was hydrogenated at 100 psi. After completion of the reaction, reaction mixture was filtered and acetic acid was distilled under reduced pressure. Residue was dissolved in DM water (75 ml). pH was adjusted to 11.0–12.0 with 50% aqueous sodium hydroxide solution. The product was extracted with methylene chloride (2×75 ml) and washed with DM water (75 ml). The methylene chloride layer was concentrated under reduced pressure to obtain 10.1 g of 1-methyl-2-oxo-3-phenylpiperazine.

$^1$H NMR (300 MHz) in CDCl$_3$: δ(ppm); 1.99 (bs, 1H), 3.04 (s, 3H), 3.05–3.19 (m, 2H), 3.31–3.56 (m, 2H), 4.58 (s, 1H), 7.27–7.43 (m, 5H).

PREPARATION OF 1-METHYL-3-PHENYLPIPERAZINE

Lithium aluminium hydride (3.04 g, 0.8 moles) was suspended in tetrahydrofuran (60 ml) under nitrogen atmosphere. A solution of 1-methyl-2-oxo-3-phenylpiperazine (10 g in 10 ml of tetrahydrofuran) was added at 10–15° C. Slowly, raised the temperature of reaction mass and refluxed for 2 hours. Cooled the reaction mass to 5° C. and quenched successively with 3 ml of water, 3 ml of 15% aqueous sodium hydroxide solution and 9 ml of water. Reaction mass was stirred for 1 hour at 25–30° C. Filtered the reaction mass and the filtrate was concentrated under reduced pressure. Dissolved the residue in DM water (25 ml) and concentrated hydrochloric acid (8 ml) and the solution was washed with cyclohexane (20 ml). pH was adjusted to 11.0–12.0 with 50% w/w aqueous sodium hydroxide solution and extracted the product with methylene chloride (2×50 ml). Methylene chloride layer was concentrated under reduced pressure and 7.54 g of pure 1-Methyl-3-phenylpiperazine was isolated in cyclohexane having HPLC purity 99.7%.

$^1$H NMR (300 MHz) in CDCl$_3$: δ(ppm); 1.80 (bs, 1H), 1.95–2.18 (m, 2H), 2.31 (s, 3H), 2.79–3.12 (m, 4H), 3.85–3.89 (m, 1H), 7.23–7.40 (m, 5H).

We claim:

1. A piperazine derivative compound represented by Formula II below

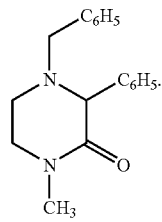

Formula II

2. A process for preparing 1-Methyl-3-phenylpiperazine represented by Formula I

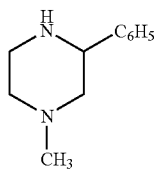

which comprises the steps of,
   reducing the compound of Formula II

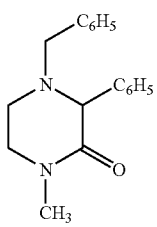

to obtain a compound of Formula VII

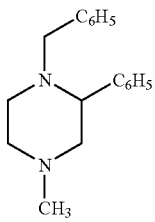

and hydrogenating the compound of Formula VII.

3. The process of claim 2, wherein the reducing step is conducted with lithium aluminum hydride.

4. The process of claim 2, wherein the hydrogenation step is conducted in acetic acid in the presence of palladium-carbon catalyst.

5. A process according to claim 2, wherein compound of Formula II

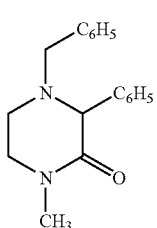

is prepared by methylation 4-benzyl-2-oxo-3-phenylpiperazine of Formula VI

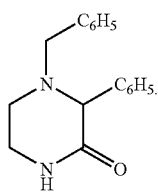

6. The process of claim 5, wherein the said methylating step is conducted with methyl iodide in N,N-dimethylformamide in the presence of sodium hydride.

7. A process for preparing 1-Methyl-3-phenylpiperazine represented by Formula I

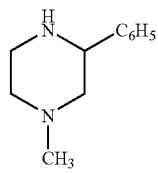

which comprises the steps of,
   hydrogenating compound of Formula II

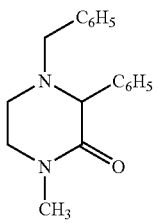

to prepare a compound of Formula VIII

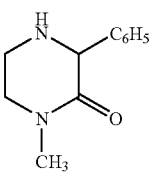

and reduction of compound of Formula VIII.

8. The process of claim 7, wherein the hydrogenation step is conducted in acetic acid in the presence of palladium-carbon catalyst.

9. The process of claim 7, wherein the reducing step is conducted with lithium aluminum hydride.

10. A process according to claim 7, wherein compound of Formula II is prepared by methylation of 4-benzyl-2-oxo-3-phenylpiperazine of Formula VI

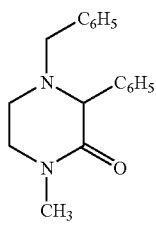

Formula II

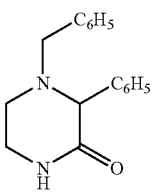

Formula VI with methyl iodide in N,N-dimethylformamide in the presence of sodium hydride.

11. The process of claim 10, wherein the said methylating step is conducted with methyl iodide in N,N-dimethylformamide in the presence of sodium hydride.

12. The process to claim 2, further comprising conversion of 1-methyl-3-phenylpiperazine of Formula I

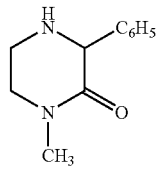

Formula I to Mirtazapine.

13. The process according to claim 7, further comprising conversion of 1-methyl-3-phenylpiperazine of Formula I

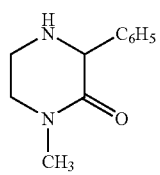

Formula I to Mirtazapine.

* * * * *